(12) United States Patent
Siefert et al.

(10) Patent No.: US 12,129,907 B2
(45) Date of Patent: Oct. 29, 2024

(54) PNEUMATIC STRUCTURE AND ASSOCIATED PRODUCTION METHOD

(71) Applicants: PARIS SCIENCES ET LETTRES—QUARTIER LATIN, Paris (FR); CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR); SORBONNE UNIVERSITÉ, Paris (FR); UNIVERSITÉ DE PARIS, Paris (FR)

(72) Inventors: Emmanuel Siefert, Paris (FR); Benoît Roman, Ivry sur Seine (FR); José Bico, Paris (FR); Etienne Reyssat, Antony (FR)

(73) Assignees: PARIS SCIENCES ET LETTRES—QUARTIER LATIN, Paris (FR); CENTRE NATIONAL DE LA RECHERCHE SCIENTIFIQUE—CNRS, Paris (FR); ECOLE SUPERIEURE DE PHYSIQUE ET DE CHIMIE INDUSTRIELLES DE LA VILLE DE PARIS, Paris (FR); SORBONNE UNIVERSITÉ, Paris (FR); UNIVERSITÉ DE PARIS, Paris (FR)

( * ) Notice: Subject to any disclaimer, the term of this patent is extended or adjusted under 35 U.S.C. 154(b) by 765 days.

(21) Appl. No.: 17/262,402

(22) PCT Filed: Jul. 22, 2019

(86) PCT No.: PCT/EP2019/069707
§ 371 (c)(1),
(2) Date: Jan. 22, 2021

(87) PCT Pub. No.: WO2020/020839
PCT Pub. Date: Jan. 30, 2020

(65) Prior Publication Data
US 2022/0341479 A1    Oct. 27, 2022

(30) Foreign Application Priority Data
Jul. 23, 2018    (FR) .................................... 1856800

(51) Int. Cl.
*F16F 9/04*    (2006.01)
(52) U.S. Cl.
CPC .......... *F16F 9/0418* (2013.01); *F16F 9/0409* (2013.01); *F16F 9/049* (2013.01)
(58) Field of Classification Search
CPC ........ F16F 9/0409; F16F 9/049; F16F 9/0418; E04H 2015/204; A47C 27/10;
(Continued)

(56) References Cited

U.S. PATENT DOCUMENTS

| 5,118,555 A | * | 6/1992 | Horovitz | ................. F16F 1/377 |
| | | | | 139/390 |
| 5,421,044 A | * | 6/1995 | Steensen | ................ A47C 27/18 |
| | | | | 5/713 |

(Continued)

FOREIGN PATENT DOCUMENTS

| CN | 102578716 A | 7/2012 |
| FR | 2968726 A1 | 6/2012 |

(Continued)

*Primary Examiner* — Robert A. Siconolfi
*Assistant Examiner* — San M Aung
(74) *Attorney, Agent, or Firm* — WC&F IP (57) ABSTRACT

The structure (10) comprises an elastically deformable body (12) defining at least one network of internal cavities (14), each internal cavity (14) having a closed contour in at least one section of the internal cavity (14).

(Continued)

Each internal cavity (14) is able to be pressurized so as to make the elastically deformable body (12) pass from a rest configuration to at least one pressurized configuration.

In each pressurized configuration, the elastically deformable body (12) has a macroscopic metric that is distinct from its macroscopic metric in the rest position.

In each pressurized configuration, the radius of curvature of an outer surface of the elastically deformable body (12), considered regarding each internal cavity (14) adjacent to the outer surface, is greater than twice the size of the internal cavity (14) adjacent to the outer surface.

17 Claims, 10 Drawing Sheets

(58) Field of Classification Search
CPC .......... A61B 17/02; A61B 2017/00557; A61B 2017/0212; A61F 2/02; A61F 2/34; A61F 2250/0004
USPC ...................................................... 267/64.27
See application file for complete search history.

(56) References Cited

U.S. PATENT DOCUMENTS

| | | | | |
|---|---|---|---|---|
| 6,098,223 | A * | 8/2000 | Larson | A47C 27/088 5/713 |
| 6,775,868 | B1 * | 8/2004 | Mileti | A47C 27/001 5/710 |
| 7,536,740 | B1 * | 5/2009 | Swartz | A47C 27/081 5/725 |
| 2005/0278861 | A1 * | 12/2005 | Kasatshko | A47C 27/082 5/713 |
| 2007/0186349 | A1 * | 8/2007 | Lipman | A47C 27/10 5/709 |
| 2010/0143130 | A1 * | 6/2010 | Cairo | F03D 1/065 29/889.72 |
| 2011/0154574 | A1 * | 6/2011 | Hrubant | A47C 27/10 156/60 |
| 2017/0035498 | A1 | 2/2017 | Boden et al. | |

FOREIGN PATENT DOCUMENTS

| | | |
|---|---|---|
| GB | 1268368 A | 3/1972 |
| WO | 03094666 A2 | 11/2003 |

* cited by examiner

PNEUMATIC STRUCTURE AND ASSOCIATED PRODUCTION METHOD

The present invention relates to a pneumatic structure comprising an elastically deformable body defining at least one network of internal cavities, each internal cavity having a closed contour in at least one section of the internal cavity, each internal cavity being capable of being pressurized so as to cause the elastically deformable body to pass from a rest configuration to at least one pressurized configuration.

Such a structure is intended to be used in order to form three-dimensional objects having a predefined structure, based on a reference shape or form, by applying a positive or negative internal pressure in the internal cavities of the elastically deformable body.

The three-dimensional objects are, for example, biomedical equipment items or units, recreational or rehabilitation equipment items or units, parts of furniture, or even industrial structures.

In a number of fields, it is highly desirable to have structures that at rest exhibit a contracted configuration which is compact, and during their use, occupy a deployed configuration, in which the structure exhibits a volume of use.

In certain cases, the structure is pneumatic. The transition from the rest configuration to the deployed configuration is achieved by inflating the structure with a fluid.

The pneumatic structures have very limited mechanical properties, in particular due to the large volume occupied by the internal cavities of the body as compared to the material comprised in the walls of the body.

In addition, these three-dimensional structures are fixed and generally prove to be difficult to bend.

Other pneumatic structures are described for example in the patent document U.S. Pat. No. 9,464,642.

These structures generally have a plurality of internal channels, which, after inflating, generate substantial deformations of the structure, such as to cause the latter to curve, elongate, contract, or twist at the time of being pressurized.

The structures described in the patent document U.S. Pat. No. 9,464,642 are for example used as pneumatic actuators. However, during the inflating of the structure, the deformation of the internal cavities is very significant. It generally occurs in only one direction and it induces an expansion at the level of the cavities which significantly deforms the structure, well beyond the macroscopic radius of curvature occupied by the structure at the level of the cavity.

Thus the forms/shapes obtained by the inflating of the structure are essentially limited by a flexion-extension type kinematics, since the deformation is almost one-dimensional, and the exterior appearance of the structure is fundamentally modified by the presence of inflated and highly deformed bubbles at the level of the cavities.

An aim of the invention is to obtain a pneumatic structure which can be easily activated in order to change form/shape rapidly and obtain a controlled and reproducible form/shape which is appropriately adapted to the desired application.

To this end, the object of the invention relates to a structure of the aforementioned type, characterized in that in each pressurized configuration, the elastically deformable body has a macroscopic metric that is distinct from its macroscopic metric in the rest configuration;

and in that, in each pressurized configuration, the radius of curvature of an exterior surface of the elastically deformable body, taken into account in relation to each internal cavity adjacent to the exterior surface, is greater than two times the size of the internal cavity adjacent to the exterior surface.

The structure according to the invention may include one or more of the following features, taken solely or according to any technically possible combination;

- in each pressurized configuration, the width of each internal cavity is less than three times, in particular less than two times, the distance from the internal cavity to the exterior surface of the elastically deformable body.
- each internal cavity is delimited laterally, in the said section, by two lateral walls, by a lower region and by an upper region of the elastically deformable body;
- in at least one section, the width of the internal cavity, taken into account between the lateral walls is less than three times the thickness of the elastically deformable body;
- in at least one section, the thickness of the lower region or/and the thickness of the lower region, taken opposite the internal cavity, is greater than half the width of the internal cavity, taken between the lateral walls;
- the structure comprises a plurality of adjacent internal cavities separated from one another by lateral walls the length whereof is greater than the width of the internal cavity, the lateral walls advantageously extending radially in relation to a central axis, or circumferentially around a central axis;
- the structure comprises a plurality of adjacent internal cavities separated from one another by pillars, the distance between the exterior surfaces of the pillars is less than two times the thickness of the upper and lower region;
- at least one internal cavity of the elastically deformable body is capable of receiving a pressure in a range between the opposite of atmospheric pressure and four times the elastic modulus of the elastically deformable body, the elastically deformable body having a first macroscopic metric when the pressure applied is the opposite of atmospheric pressure, and a second macroscopic metric that is distinct from the first macroscopic metric when the pressure applied is four times the elastic modulus;
- each internal cavity in each pressurized configuration has a section with an area that is less than 400% of the area of the section of the internal cavity in the rest configuration;
- the structure comprises an internal reinforcing framework deployable between a contracted state and a deployed state during the transition of the elastically deformable body passing from the rest configuration to the pressurized configuration, the internal reinforcing framework having in the deployed state an elastic modulus that is greater than that of the elastically deformable body in order to stiffen the elastically deformable body, the thickness of the internal reinforcing framework being advantageously at least 10 times smaller than the greatest dimension of the internal reinforcing framework;
- the internal reinforcing framework includes a network of wires that is unstretched in the contracted state and stretched in the deployed state, or at least one tier of inextensible sheeting cut-out, in particular with interlocking fork-shaped patterns;
- the structure comprises a first network of internal cavities that is capable of being pressurized, and at least a second network of internal cavities that is capable of being pressurized independently of the first network of internal cavities, the first network of internal cavities and the second network of internal cavities being advantageously tiered;

the structure forms a biomedical equipment item/unit, a recreational and/or rehabilitation equipment item/unit, a furniture component, an industrial equipment item/unit having an adaptable form or shape, in particular an adjustable headrest or a wind turbine blade;

the elastic modulus of the elastically deformable body is between 50 kPa and 200 MPa;

in the rest configuration, the elastically deformable body is a plate;

in the rest configuration, the elastically deformable body possesses a three-dimensional form/shape having one small dimension, that is typically 10 times smaller, than the other two dimensions, the three-dimensional form/shape being in particular a shell;

in the rest configuration, the elastically deformable body is a volume;

the body is provided with a thin layer of chiseled rigid material;

the chiseled rigid material is chosen from wood, plastic, metal, and/or linoleum;

the elastically deformable body is produced from an elastomer-based material, in particular polyurethane, silicone, natural latex, and mixtures thereof;

the thickness of the elastically deformable body is less than 1 m and is in particular comprised between 0.01 mm and 100 mm The invention also relates to a production method for producing a structure as defined here above, comprising of the following steps:

moulding of a first part of the elastically deformable body presenting each internal cavity, with each internal cavity being open;

closing of each internal cavity by means of applying a second part of the elastically deformable body over the first part of the elastically deformable body.

The method according to the invention may include one or more of the following characteristic features, taken solely or according to any technically possible combination:

the method comprises, at the time of molding, the incorporation of an internal reinforcing framework deployable between a contracted state and a deployed state during the transition of the elastically deformable body passing from the rest configuration to the pressurized configuration, with the internal reinforcing framework in the deployed state locking-in the elastically deformable body in the pressurized configuration.

The invention also relates to a shaping method for shaping a three-dimensional object that includes the following steps:

providing of a pneumatic structure as defined here above, with a first pressure being applied in the internal cavities, and the elastically deformable body having a first configuration;

modification of the pressure applied in the internal cavities, in order to obtain a second configuration of the elastically deformable body, the macroscopic metric of the elastically deformable body being modified, the radius of curvature of an exterior surface of the elastically deformable body, taken in the second configuration, opposite each internal cavity adjacent to the surface, is greater than two times the size of the internal cavity adjacent to the surface, taken at the level of the closed contour section.

The forming-shaping method may include one or more of the following characteristic features, taken solely or according to any technically possible combination:

the first configuration is a rest configuration, with the second configuration being a pressurized configuration;

the structure comprises a reinforcing framework that is accommodated in the elastically deformable body, the transition from the first configuration to the second configuration inducing the transition of a reinforcing framework present in the elastically deformable body from a contracted state to a deployed state when tensioned thereby locking in the structure.

The object of the invention also relates to a pneumatic structure comprising an elastically deformable body that defines a plurality of internal cavities, each internal cavity being delimited laterally over at least one section by two lateral walls and being delimited by a lower region and by a lower region of the elastically deformable body, each internal cavity being capable of being pressurized so as to cause the elastically deformable body to pass from a rest configuration to at least one pressurized configuration, characterized in that in each pressurized configuration, the elastically deformable body has a macroscopic metric that is distinct from its macroscopic metric in the rest configuration;

the structure comprising an internal reinforcing framework deployable between a contracted state and a deployed state during the transition of the elastically deformable body passing from the rest configuration to the pressurized configuration, the internal reinforcing framework having in the deployed state an elastic modulus that is greater than that of the elastically deformable body in order to stiffen the elastically deformable body.

The structure thus defined does not necessarily include the characteristic feature which specifies that, in each pressurized configuration, the radius of curvature of an exterior surface of the elastically deformable body, taken opposite each internal cavity adjacent to the exterior surface, is greater than two times the size of the internal cavity adjacent to the exterior surface.

The structure thus defined may include one or more of the characteristic features defined here above, taken into consideration in isolation or in accordance with any technically possible combination.

The invention will be better understood upon reading the description which follows, provided solely by way of example, and made with reference to the appended drawings, in which.

A first pneumatic structure 10 according to the invention is illustrated schematically in FIGS. 1 to 6.

Figures 1, 2:
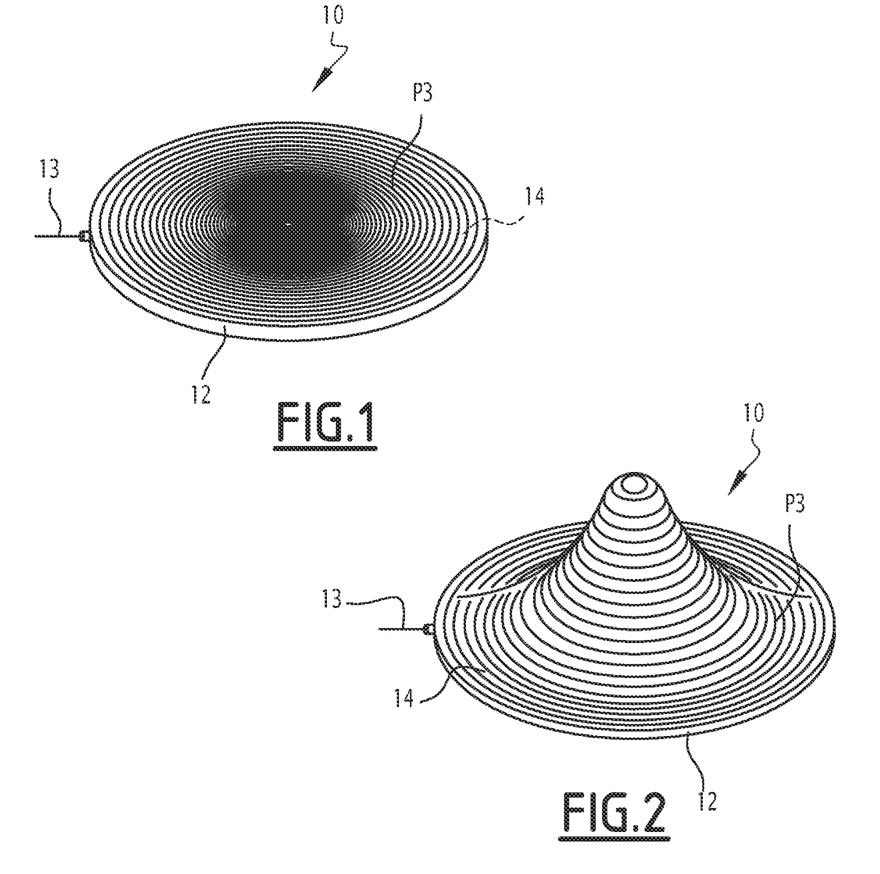
FIG. 1 is a view of a first pneumatic structure according to the invention, in a rest configuration.
FIG. 2 is a view analogous to that in FIG. 1, in a first pressurized configuration, in which a positive pressure is applied in the pneumatic structure.
Figure 3:
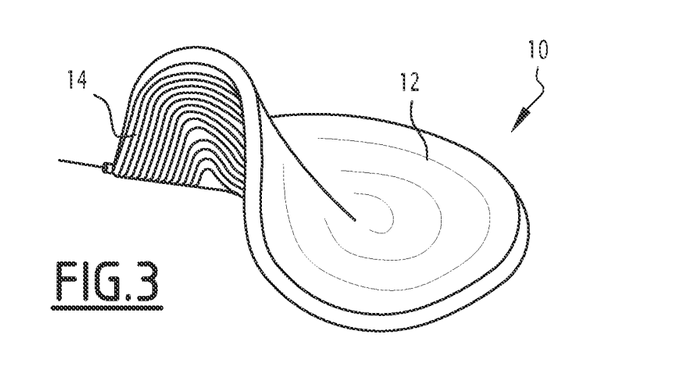
FIG. 3 is view analogous to that in FIG. 1, in a second pressurized configuration, in which negative pressure is applied in the pneumatic structure.

The structure 10 comprises an elastically deformable body 12 which defines within its interior a plurality of internal cavities 14, that are capable of being pressurized so as to cause the elastically deformable body 12 to pass from a rest configuration, shown in FIG. 1, to a plurality of pressurized configurations, two examples of which are represented in FIGS. 2 to 3.

The structure 10 in addition comprises at least one pressurizing port 13, that communicates with the internal cavities 14 in order to enable the pressurization of the cavities 14.

As will be described in detail here below, the elastically deformable body 12 is configured, by means of the structure of the internal cavities 14 that it contains, so as to deform in a reversible manner between its rest configuration, which is advantageously planar, and each pressurized configuration, in which it adopts a three-dimensional form/shape that exhibits at least in part a non-zero Gaussian curvature, the macroscopic metric of the elastically deformable body 12 in the pressurized configuration being different from the macroscopic metric of the elastically deformable body 12 in the rest configuration.

The term "macroscopic metric of the elastically deformable body" is understood to refer to the set of distances separating two different points P1, P2 of the median surface S (see FIGS. 5 and 6) defined within the elastically deformable body 12 between its upper surface 14A and its lower surface 14B.

Thus, at least certain distances between the different points P1, P2 of the median surface S have varied during the transitioning from the rest configuration to the pressurized configuration.

More generally, the macroscopic metric is advantageously defined as the set of all the distances determined between the centers of the internal cavities 14.

In the case of a non-convex cavity, the latter is further broken down into a plurality of sub-cavities of which the centers constitute as many points of reference for the said definition.

Thus, if the macroscopic metric is modified, this signifies that there exists a sub-cavity breakdown for which the distance between the centers of at least two cavities is modified.

Similarly, with reference to FIGS. 1 and 2, at at least one point on the median surface S, the Gaussian curvature is zero in the rest configuration and is non-zero, for example positive or negative, in the pressurized configuration.

The term "Gaussian curvature" or "Gauss curvature" is understood to refer to the product of the principal radii of curvature at a given point on a surface. By way of example, the Gaussian curvature of a sheet that is planar or rolled up in a cone or cylinder is zero. It is positive for a sphere and negative for a saddle.

The elastically deformable body 12 is produced for example from an elastomer having an elastic modulus, as measured at 23° C. in accordance with the standard NFT 46-002, comprised between 10 kPa and 200 MPa.

In this example, the elastically deformable body 12 is produced for example from polyurethane, silicone, natural latex, or any other natural or artificial elastomer or mixtures thereof.

Figure 5:
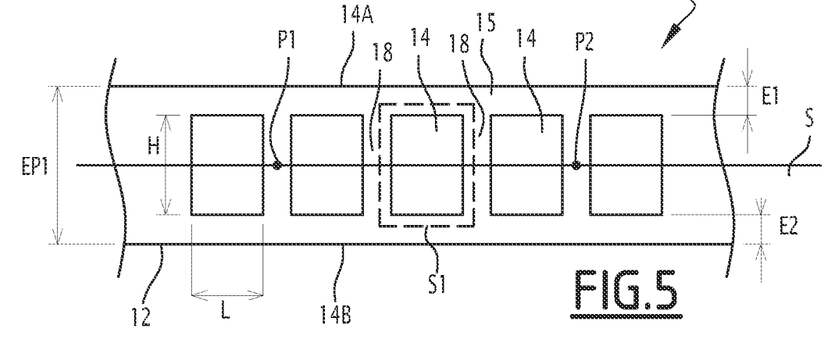
FIG. 5 is a schematic cross-sectional view of a detail of the structure perpendicular to the median plane, in the rest configuration.

In the example illustrated in FIG. 5, the elastically deformable body 12 exhibits a form in the shape of a plate or a shell in its rest configuration.

It comprises at least one solid upper region 15, at least one solid lower region 16, and between the upper region 15 and the lower region 16, a plurality of intermediate walls 18 situated at a distance from one another.

In this example, the walls 18 are formed by partitions which have a longitudinal extension (the perimeter thereof in FIG. 4) that is greater than the height H thereof, taken between the upper region 15 and the lower region 16, in particular at least 10 times greater than the height H thereof at the periphery of the elastically deformable body 12.

Figure 4:
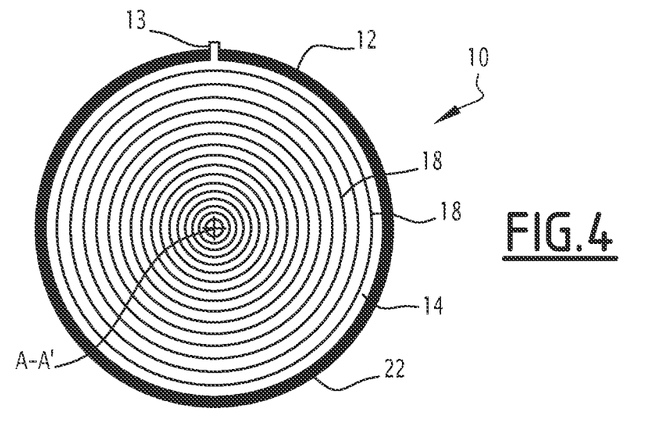
FIG. 4 is a view, taken from a cross-sectional perspective in a median plane of the structure shown in FIG. 1, that illustrates the configuration of the internal cavities present in the structure.

In the example represented in FIG. 4, the walls 18 extend concentrically from a central axis A-A' of the structure 10, towards the periphery 22 of the structure 10.

Figure 6:
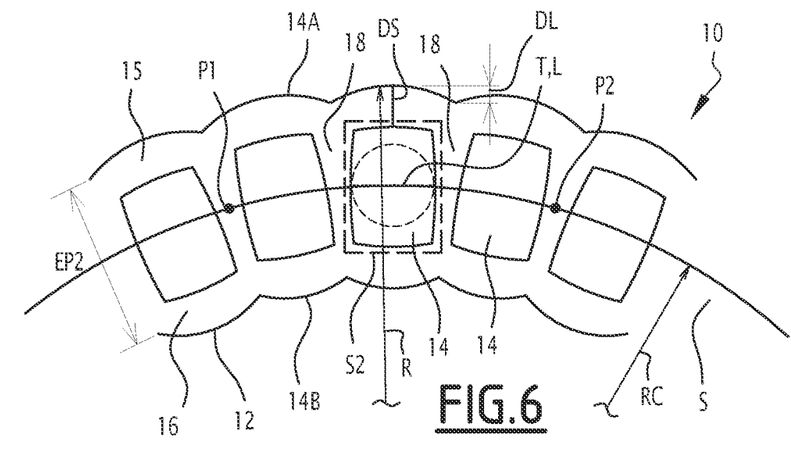
FIG. 6 is a view analogous to that in FIG. 5, in the first pressurized configuration.

With reference to FIGS. 5 and 6, each cavity 14 is delimited, in at least one transverse section of the cavity, laterally by two walls 18 facing each other. Each cavity 14 is delimited above the walls 18 by the upper region 15, and below the walls 18 by the lower region 16.

Each cavity 14 has in this section a closed contour, which, in this particular example, is polygonal in the rest configuration. The section of the cavity 14 is elongated between the upper region 15 and the lower region 16.

Thus, in the rest configuration, the height H of the cavity 14 is greater than the width L of the cavity 14, in particular at least two times greater than the width L of the cavity 14.

Similarly, the height H of the cavity 14 is greater than two times the thickness E1 of the upper region 15.

The height H of the cavity 14 is also greater than two times the thickness E2 of the lower region 16, in particular greater than 5 times the thickness E2.

Furthermore, the width L of the cavity 14 is less than three times the thickness EP1 of the elastically deformable body 12, taken between the upper surface 14A and the lower surface 14B.

The cavities 14 of at least one network of cavities 14 are interconnected to each other. In this example, all of the cavities 14 are interconnected to each other.

In addition, each network of cavities 14 interconnected to each other moreover is connected to a port 13 in order to enable the selective pressurization thereof.

The ratio of the volume of the cavities 14 to the volume of material in the elastically deformable body 12 is advantageously less than 50%, in particular comprised between 5 and 30%.

With reference to the particular example represented in FIG. 1, in the rest configuration, the elastically deformable body 12 is flat and forms a plate. The Gaussian curvature of each point of the median surface is zero.

In the first pressurized configuration, represented in FIG. 2, a positive pressure has been introduced into the cavities 14 of the elastically deformable body 12.

This positive pressure has generated anisotropic stresses within the elastically deformable body 12, in particular at the level of the regions 15 and 16. These stresses have produced a locally weak deformation of the structure of the cavities 14, which causes a significant macroscopic deformation of the elastically deformable body 12 so as to generate a three-dimensional form of which at least a portion of the points have a non-zero Gaussian curvature, in this instance a positive Gaussian curvature at its topmost point, and negative at the edges.

The macroscopic deformation of the elastically deformable body 12 has led to a variation in the metric on the median surface S.

According to the invention, in each pressurized configuration, the radius of curvature R of the upper surface 14A or/and of the lower surface 14B of the elastically deformable body 12, defined as the minimum of the two principal radii of curvature of the surface 14A, 14B, taken opposite each internal cavity 14 adjacent to the surface 14A, 14B, is greater than two times the size of the cavity 14 adjacent to the surface 14A, 14B.

The size T of the cavity 14 is defined as the diameter of the largest sphere which can be inserted into the cavity 14 without deformation.

Similarly, the width L of each internal cavity 14 adjacent to the exterior surface 14A, 14B is less than two times the distance DS from the internal cavity 14 to the exterior surface 14A, 14B of the elastically deformable body 12 that is closest to the internal cavity 14.

In order to determine the distance DS for each internal cavity 14, it is necessary to define the shortest segment which connects the internal surface of the cavity and the exterior surface of the elastically deformable body, the distance DS being the length of this segment. The width L of the cavity is defined as the smallest of the widths of the internal cavity 14 measured perpendicularly to the aforementioned segment.

The term "cavity adjacent to the surface" in this instance is understood to refer to a cavity in which the segment DS which connects them to the surface does not pass through any other cavity.

The aforementioned properties are verified in particular when the pressure applied in the pressurized configuration is the opposite of atmospheric pressure and also when the pressure applied in the pressurized configuration is four times the elastic modulus of the material from which the elastically deformable body is formed.

In this example where the structure 10 is in the form of a plate, the macroscopic radius of curvature RC of at least one region of the elastically deformable body 12 comprising the cavities 14 has decreased so as to have a non-infinite value, however greater than three times the thickness of the elastically deformable body 12.

The minimum macroscopic radius of curvature within the structure is in particular less than 10 cm and is for example comprised between 1.5 cm and 2 m. The macroscopic radius of curvature is defined as the minimum of the two local principal radii of curvature of the median surface S in the pressurized configuration.

On the contrary, the local deflection DL of the upper region 15 of the body 12 (see FIG. 6) and of the lower region 16 of the body 12 opposite each cavity 14 continued to be limited.

Thus, the local deflection DL of the elastically deformable body 12 in relation to each internal cavity 14 in each pressurized configuration is less than at least 5 times the macroscopic radius of curvature of the body, taken opposite the internal cavity.

The local deformation DL is determined respectively on the upper surface 14A and on the lower surface 14B, as the local height of each bump that is formed in relation to each cavity 14.

The maximum variation in the area of the section of the cavity 14 is less than 400% between the area of the section SE2 of the cavity 14 in the pressurized configuration and the area of the section SE1 of the cavity 14 in the pressurized configuration. This ensures a macroscopic deformation of the body 12, by minimising the deformation at the level of each cavity 14.

The maximum variation in thickness of the body 12, taken into account between the thickness EP2 measured in the pressurized configuration and the thickness EP1 measured in the rest configuration is less than 100% and is in particular comprised between 5% and 50%.

Thus, a desired and pre-programmed form/shape of the structure 10 is obtained simply and rapidly in each pressurized configuration, without the external appearance of structure 10 being deteriorated, since the out-of-plane expansion of the cavities 14 is very limited within the body 12 in order to promote the macroscopic deformation within the plane of the structure 10 and to obtain a variation in macroscopic metric.

In the example represented in FIG. 2, the elastically deformable body 12 thus exhibits a dome shaped form in the pressurized configuration, with positive pressure.

As illustrated in FIG. 3, in a second pressurized configuration when negative pressure is applied within the interior of the cavities 14 of the body 12, at least a portion of the points of the median surface have a negative Gaussian curvature, and the elastically deformable body 12 then occupies a horse saddle shaped form.

Figure 7:
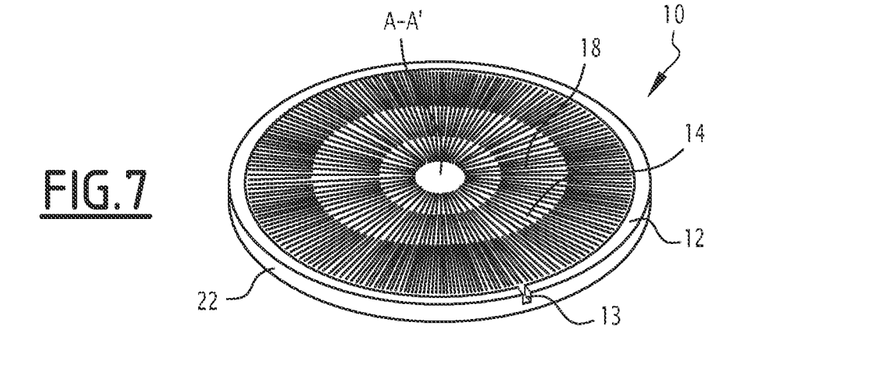
FIGS. 7 to 15 illustrate variants of structures according to the invention in the rest configuration and in a pressurized configuration.
Figure 8:
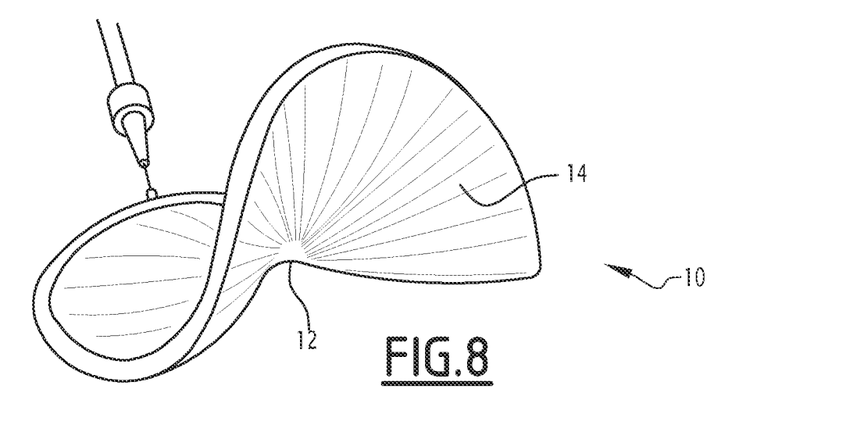

In the variant represented in FIGS. 7 and 8, the walls 18 laterally delimiting the cavities 14 extend radially from a central axis A-A' of the elastically deformable body 12 towards the periphery 22.

Unlike the structure 10 represented in FIG. 4, the application of a positive pressure so as to pass into the first pressurized configuration causes the elastically deformable body 12 to adopt a horse saddle shaped form, as illustrated in FIG. 8, On the contrary, the application of negative pressure so as to pass into the second pressurized configuration causes the elastically deformable body 12 to adopt a dome shaped form.

Figure 9:
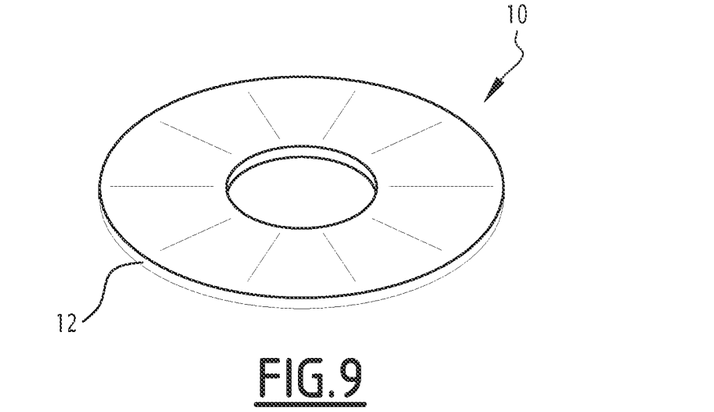
Figure 10:
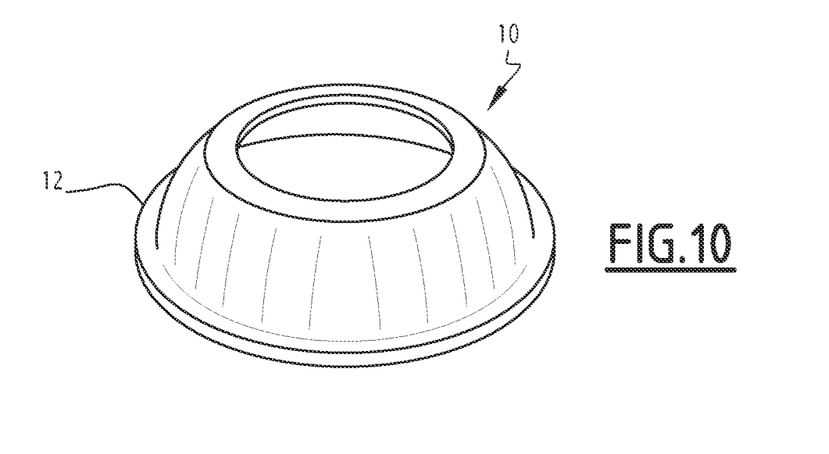

In the variant represented in FIG. 9, a central through hole 30 is provided in the center of the elastically deformable body 12. In the pressurized configuration represented in FIG. 10, the elastically deformable body 12 thus adopts a truncated dome shaped form.

Figure 11:
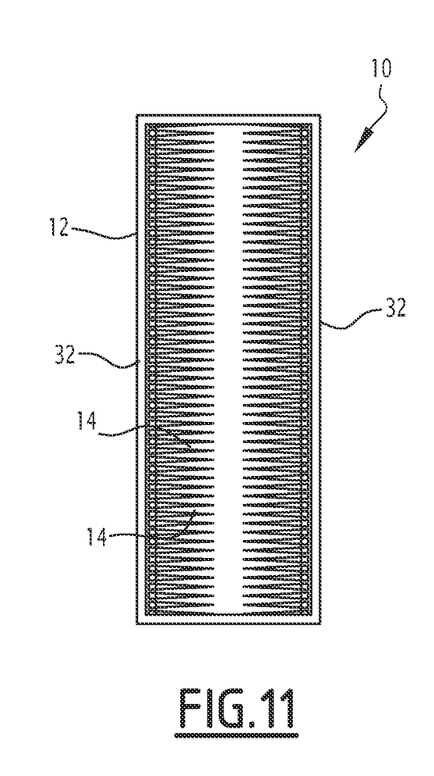

In the variant represented in FIG. 11, the elastically deformable body 12 has a substantially rectangular shaped form in the rest configuration. The cavities 14 are arranged in the lateral regions 32 of the elastically deformable body 12, perpendicularly to a longitudinal axis B-B' of the elastically deformable body 12. On the contrary, the central region 34 of the elastically deformable body 12 is completely devoid of cavities 14.

Figure 12:
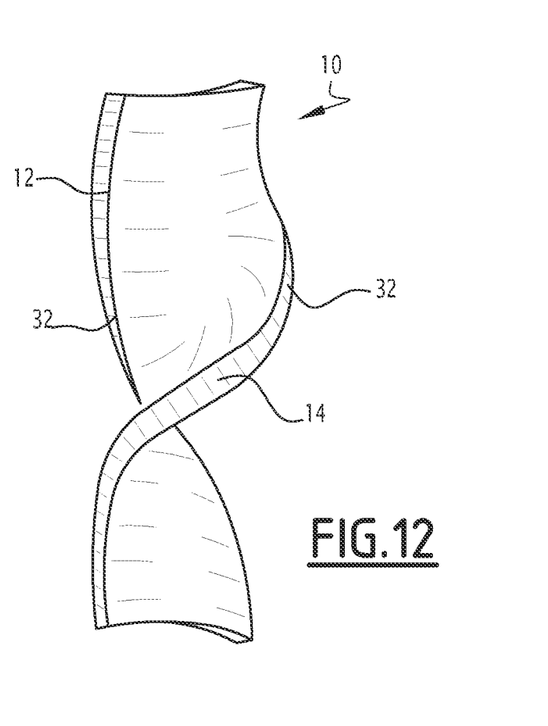

As illustrated in FIG. 12, the application of pressure in the cavities 14 causes a torsional deformation of the lateral regions 32 of the elastically deformable body 12, the torsion being in one direction along a first edge 32 and in an opposite direction along an opposite edge of the elastically deformable body 12.

Figure 13:
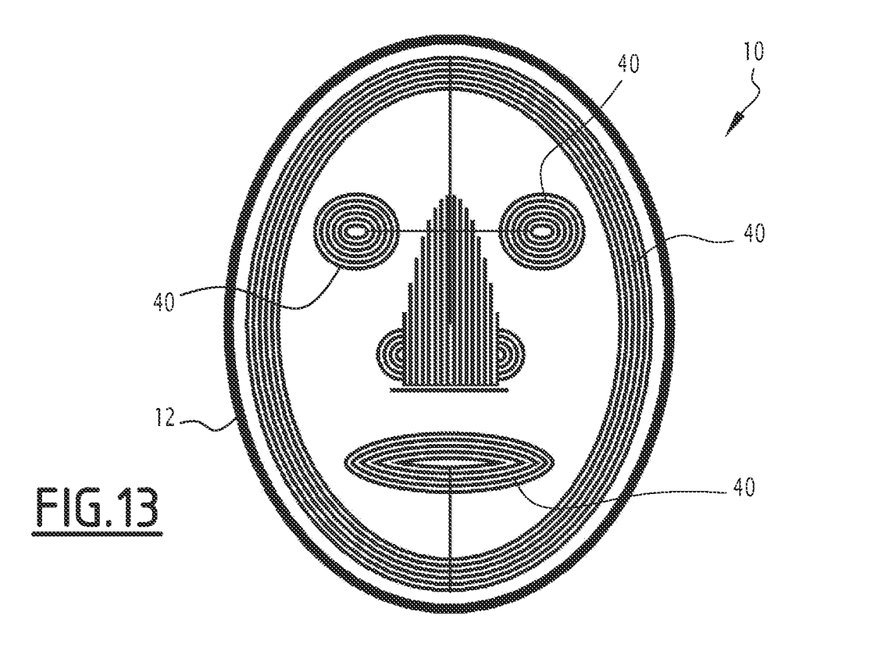
Figure 14:
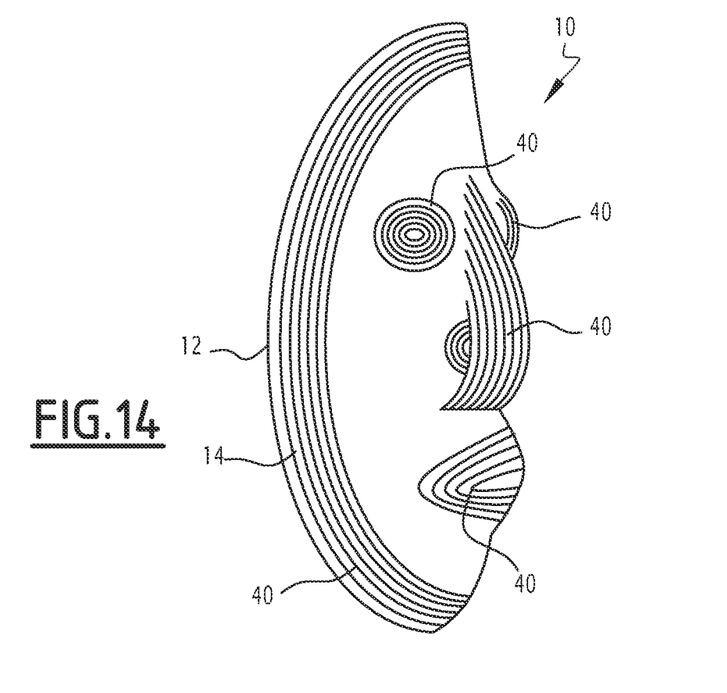

In the variant represented in FIGS. 13 and 14, the elastically deformable body 12 has selected regions 40 that are provided with cavities 14, with each region 40 being capable of generating a particularly shaped form, and the regions 42 which are devoid of any cavities 14.

For example, the elastically deformable body 12 comprises a peripheral region 40 provided with cavities, and four central regions 40 provided with cavities, that in this instance, are capable of forming respectively the mouth, the nose, and the eyes of a human face in the pressurized configuration.

Figures 15, 16:
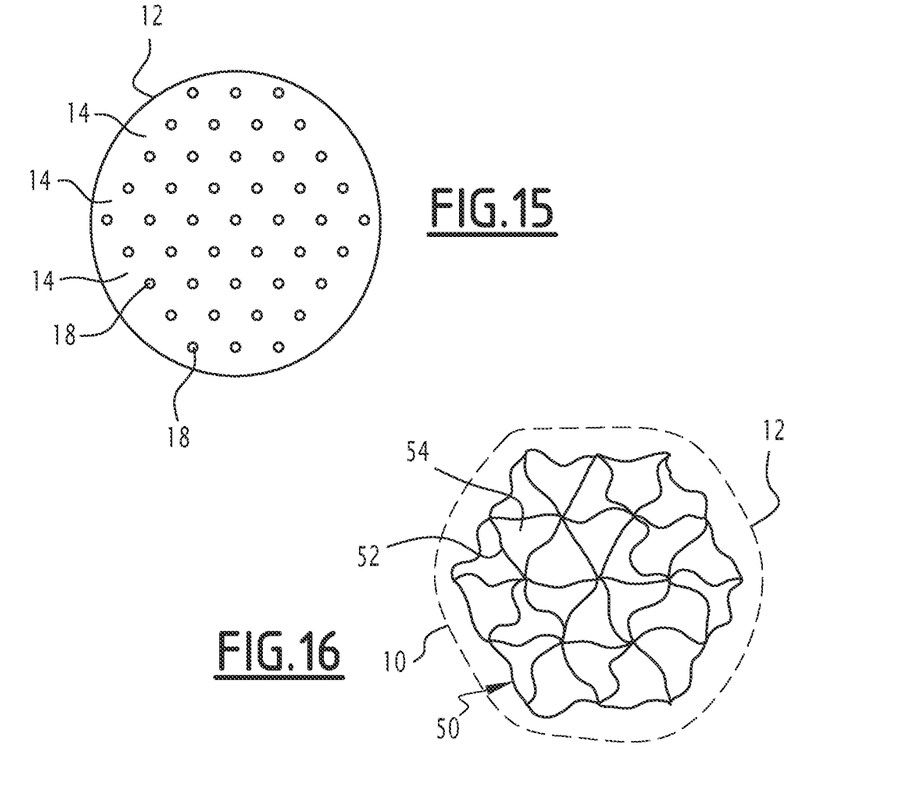
FIGS. 16 to 18 illustrate a first example of a structure according to the invention provided with a stiffening internal reinforcing framework.

In the variant illustrated in FIG. 15, the lateral walls 18 delimiting each cavity 14 are formed by pillars. The transverse extension of the pillars is generally less than 2 times the height thereof.

The functioning of the structure 10 depicted in FIG. 15 is analogous to the functioning of the structures 10 depicted in the preceding figures.

The structures 10 according to the invention are therefore easily deformable, and make it possible to obtain shapes and forms that are predetermined by the structure of the cavities 14 contained in the elastically deformable body 12.

This deformation is very rapid, thus making it possible to pass simply and in an almost immediate manner from the rest configuration to the pressurized configuration, or from a first pressurized configuration into a second pressurized configuration.

In order to produce the aforementioned structures 10, having a desirably shaped form in the pressurized configuration, it is possible to model the form/shape and the metrics of the structure 10, as well as the position of the cavities 14 necessary so as to obtain the said form/shape and the metrics desired. Thereafter, the form/shape and the corresponding metric of the structure 10 and the cavities 14 in the rest configuration are computed in order to obtain the position of the walls 18 to be formed by molding.

A mold having a form shaped so as to be complementary to the computed form/shape is made and the lower region 16 and the walls 18 are formed by means of molding.

Then, the upper region 15 is formed or is assembled over the walls 18 so as to close the cavities 14 and render the cavities 14 tightly sealed.

Figure 24:
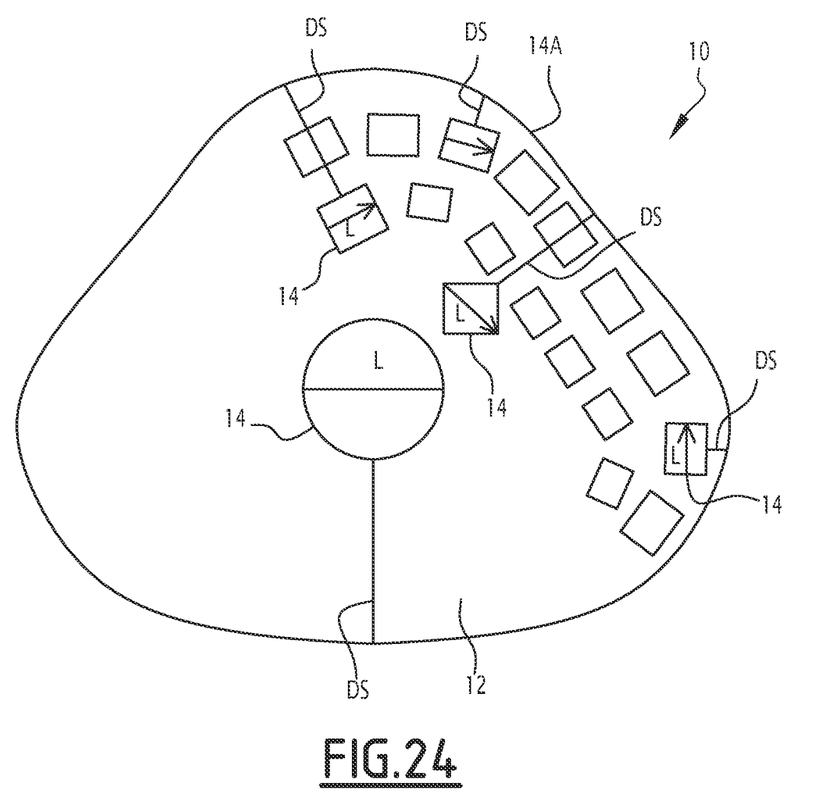
FIG. 24 illustrates another pneumatic structure according to the invention.

In one variant represented in FIG. 24, the elastically deformable body 12 has a three-dimensional volumetric form in its rest configuration.

As previously noted, in each pressurized configuration, the radius of curvature R of the exterior surface 14A of the elastically deformable body 12, defined as the minimum of the two principal radii of curvature of the exterior surface 14A, taken opposite each internal cavity 14 adjacent to the exterior surface 14A, is greater than two times the size of the cavity 14 adjacent to the exterior surface 14A.

Similarly, the width L of each internal cavity 14 adjacent to the exterior surface 14A is less than three times the distance DS from the internal cavity 14 to the exterior surface 14A of the elastically deformable body 12 that is closest to the internal cavity 14 adjacent to the exterior surface 14A, with the distance DS and the width L being defined as noted above.

Figure 25:
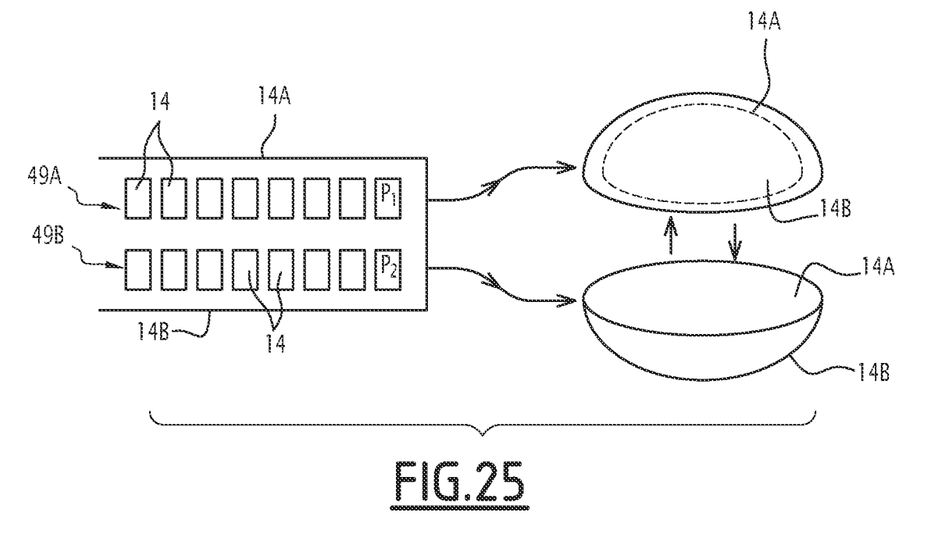
FIG. 25 illustrates yet another pneumatic structure according to the invention.

In the variant represented in FIG. 25, the elastically deformable body 12 comprises at least two networks 49A, 49B of internal cavities 14 arranged in a tiered manner one on top of the other. The networks 49A, 49B are capable of being pressurized independently of one another.

As illustrated in FIG. 25, when the first network 49A of cavities 14 is pressurized, the body 12 gets deformed along a first convexity oriented in a first direction, in which the surface 14A is convex and the surface 14B is concave. On the contrary, when the second network 49B of cavities 14 is pressurized, the body 12 gets deformed along a second convexity in a second direction that is opposite to the first direction, in which the surface 14A is concave and the surface 14B is convex.

Figures 17, 18:
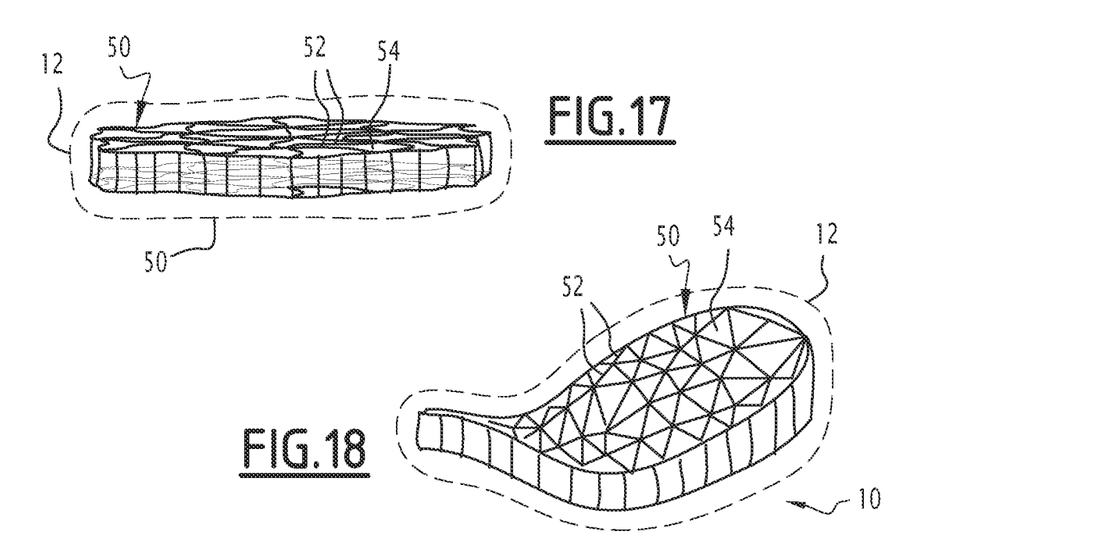

In the variant represented in FIGS. 16 to 18, the structure 10 further comprises an internal reinforcing framework 50 that is embedded in the elastically deformable body 12. The internal reinforcing framework 50 is able to be deployed between a contracted state, visible in FIGS. 16 and 17 and a deployed state, visible in FIG. 18.

In this example, the reinforcing framework 50 is formed by a network of wires 52 that define meshes 54 which are linked to each other. The thickness of the wires 52 is less than at least 10 times the length thereof.

The wires 52 have an elastic modulus, as measured by the method described here above, that is greater than the elastic modulus of the elastically deformable body 12. This elastic modulus is for example greater than 10 GPa and in particular comprised between 0.1 GPa and 1000 GPa. Thus, the wires 52 are almost inextensible.

In the contracted state, visible in FIG. 16, the wires 52 are loose and each mesh 54 has a minimum area. In the example represented in FIG. 17, the reinforcing framework 50 has a planar form corresponding to the rest configuration of the elastically deformable body 12.

In the deployed state, visible in FIG. 18, the wires 52 are stretched, Each mesh 54 has a maximum area.

The reinforcing framework 50 thus then has a rigid three-dimensional structure corresponding to the pressurized configuration of the elastically deformable body 12. The reinforcing framework 50 thus limits the expansion of the elastically deformable body 12 in this pressurized configuration.

The elastically deformable body 12 is stiffened by the stretched wires 52 of the reinforcing framework 50 which have an elastic modulus that is greater than that of the elastically deformable body 12. This structural stiffening of the elastically deformable body 12 is brought about by the effect of tensegrity.

Advantageously, the body 12 is no longer deformable to the touch in the pressurized configuration.

Figure 19:
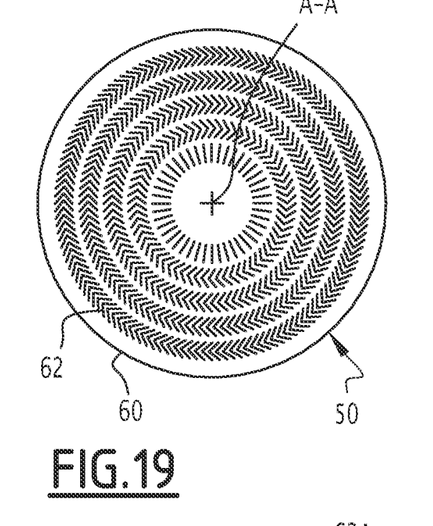
FIGS. 19 to 20 illustrate a second example of a stiffening internal reinforcing framework.

In one variant represented in FIG. 19, the internal reinforcing framework 50 comprises at least one sheet 60 of an inextensible material cut-out in lamellae motif patterns 62. In the example represented in FIG. 19, the cut-out patterns 62 have chevron shaped forms. The chevrons are in this instance arranged concentrically around the central axis A-A'.

The sheet 60 is embedded in the elastically deformable body 12.

In the contracted state, the sheet 60 is planar and corresponds to the rest configuration of the elastically deformable body 12. The branches of each chevron constituting one pattern motif 62 are brought closer to one another.

Figure 20:
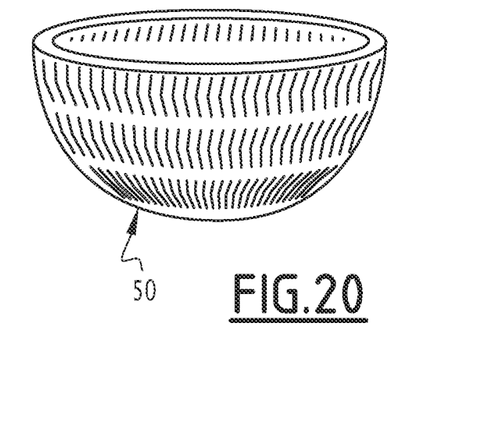

In the deployed state, visible in FIG. 20, the sheet 60 has become deformed by virtue of the cut-outs 62 in order to occupy a three-dimensional deployed state. The pattern motifs 62 are elongated, by the spacing apart of the branches of each chevron constituting a pattern motif 62. This elongation produces a stiffening of the sheet 60 and as a result, of the body 62, by the effect of tensegrity.

In one variant, the structure 10 comprises a plurality of sheets 60 that are tiered in the elastically deformable body 12.

Figure 21:
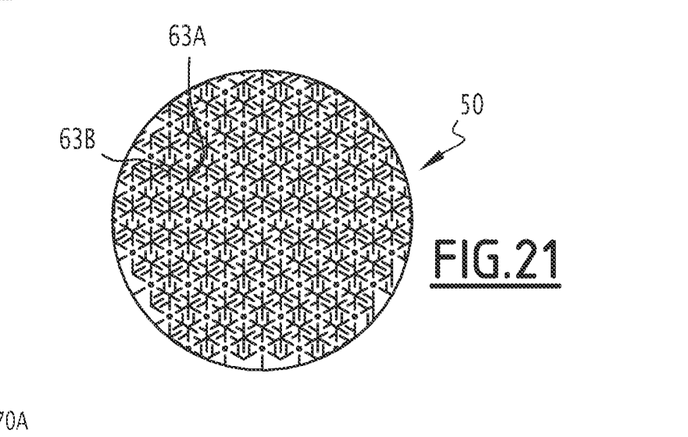
FIGS. 21 to 23 illustrate a third example of a stiffening internal reinforcing framework.
Figure 22:
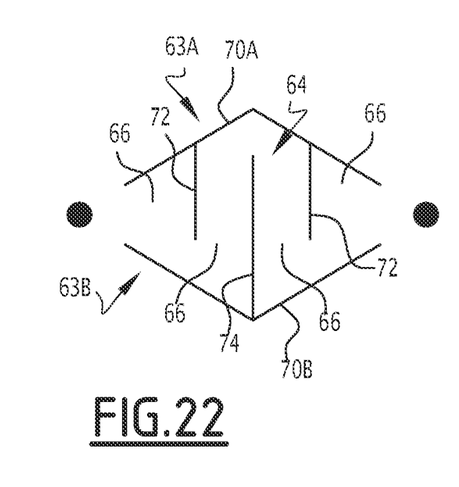
Figure 23:
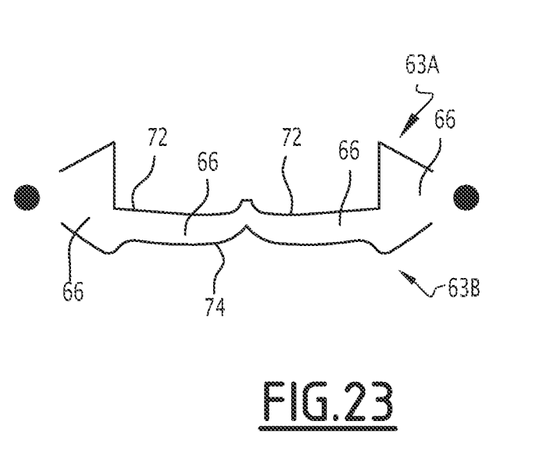

In the example represented in FIGS. 21 to 23, the cut-outs 62 have fork shaped forms 63A, 63B each interlocking with or nested within the other. The forks 63A, 63B facing each other define between them a sinuous cut-out path 64 comprising interlocking fingers 66 that are capable of passing from a configuration of being parallel to each other in the contracted state of the reinforcing framework 50 (see FIG. 22) to a configuration of being substantially aligned with each other in the deployed state of the reinforcing framework 50 (see FIG. 23).

In the example represented in FIG. 22, the fork 63A comprises a chevron 70A that opens to face another symmetrical chevron 70B of the fork 63B. The fork 63A in addition comprises, between the branches of the chevron 70A, two parallel cut-out lines 72 directed towards the other chevron 70B The fork 633 comprises between the branches of the symmetrical chevron 70B, one central cut-out line 74 interposed between the parallel cut-out lines 72.

The sinuous cut-out path 64 is delimited between the chevrons 70A, 70B, following along the cut-out lines 72, 74.

The cut-outs 62 are present in the form of repeated motif patterns throughout the sheet 60.

As previously described above, the sheet 60 is capable of passing from a contracted state, in which the interlocking fingers 66 are parallel to each other, that corresponds to the rest configuration of the elastically deformable body 12, into an deployed state, in which the interlocking fingers 66 are aligned with one another, thereby stiffening the structure 10 in a pressurized configuration.

Figure 26:
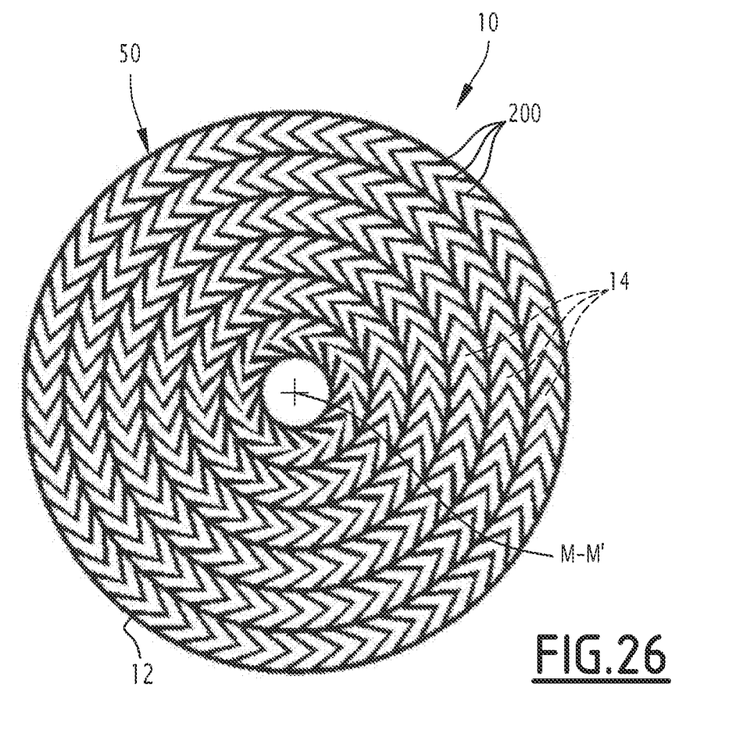
FIGS. 26 and 27 illustrate a fourth example of a stiffening internal reinforcing framework.
Figure 27:
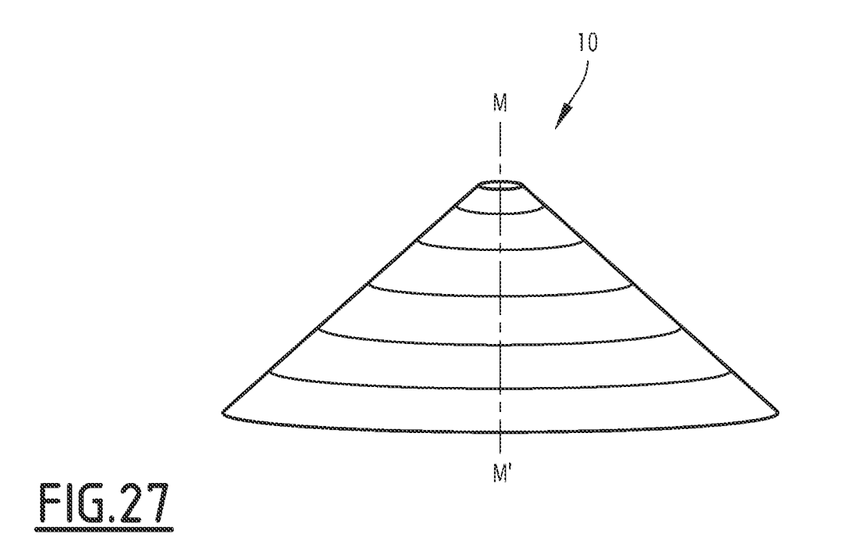

In the variant of the structure 10 illustrated in FIGS. 26 and 27, the internal reinforcing framework 50 advantageously comprises a succession of chevrons 200 distributed circumferentially.

The body 12 is elastically deformable between a rest configuration, which is advantageously planar, and at least one pressurized configuration, which in this instance, is in the form of a truncated cone, as is visible in FIG. 27. The deploying of the chevrons produces a stiffening of the reinforcing framework 50 by the effect of tensegrity.

Figure 28:
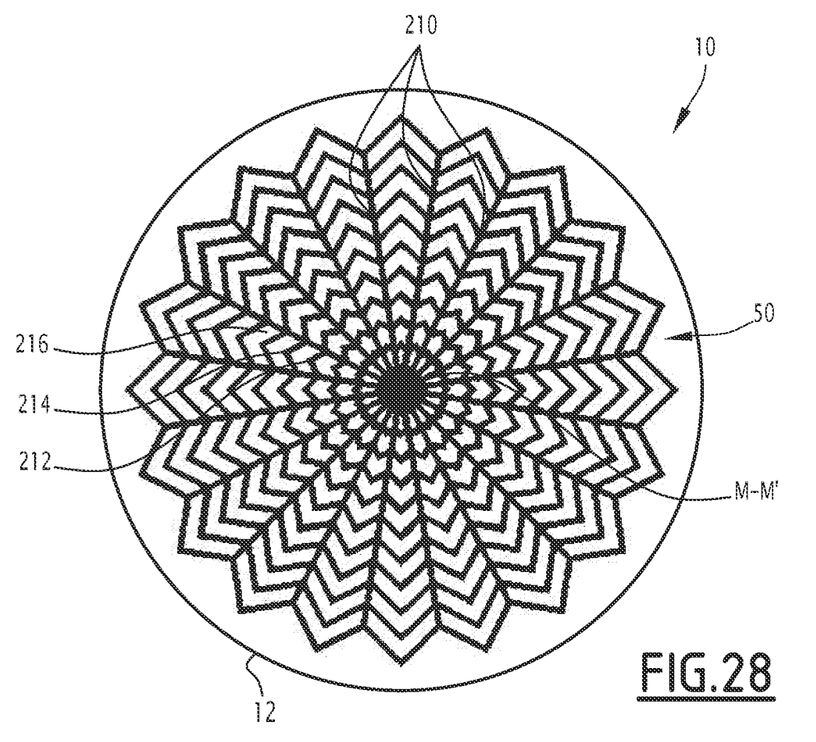
FIGS. 28 and 29 illustrate a fifth example of a stiffening internal reinforcing framework.
Figure 29:
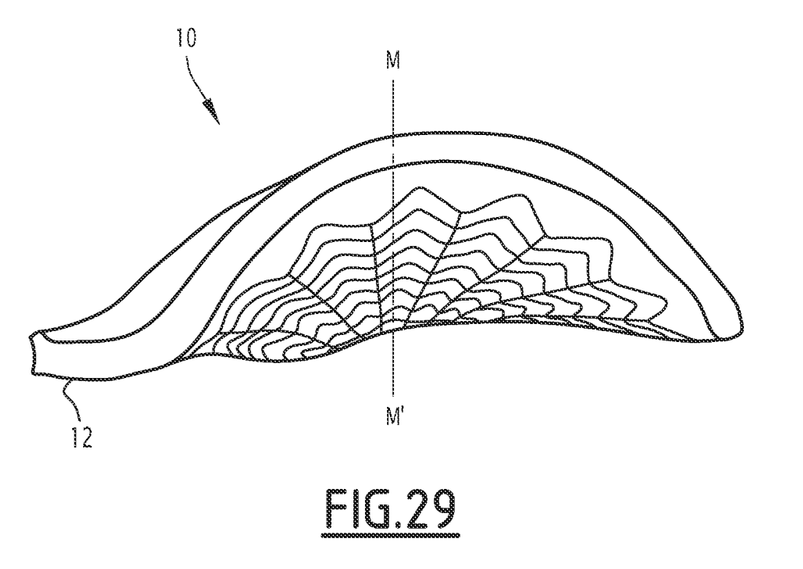

In the variant of the structure 10 illustrated in FIGS. 28 and 29, the internal reinforcing framework 50 has a general form shaped like a flake, with radial branches 210 which diverge radially from a central axis M-M'. The radial branches 210 are connected to one another by the chevrons 212, 214, 216 that extend over successive circumferences around the central axis M-M', the circumferences becoming increasingly distant from the central axis M-M'. The width of the chevrons 212, 214, 216 increases starting from the central axis M-M' outwards to the periphery of the reinforcing framework 50.

In this example, the point of the chevrons 212, 214, 216 points away from the central axis M-M'.

The body 12 is elastically deformable between a rest configuration, which is advantageously planar, and at least one pressurized configuration, which in this instance, is in a horse saddle shaped form, as is visible in FIG. 29, The deployment of the chevrons produces a stiffening of the reinforcing framework 50 by the effect of tensegrity.

In one variant of the embodiments previously described above, the structure 10 comprises a thin layer of chiseled rigid material, chosen from wood, plastic, metal, and linoleum.

The thickness of the thin layer is less than at least 10 times the thickness of the elastically deformable body 12. The chiseled rigid material gets deformed on the surface of the elastically deformable body 12 following the deformations of the elastically deformable body 12.

In one application of the structure 10, the shapes and forms, and dimensions of the elastically deformable body 12 in the rest configuration and in each of the pressurized configurations are selected, for example, so as to ensure that the structure 10 forms a biomedical equipment item or unit, in particular a deployable stent, or an actuator for handling and moving tissue. In this case, the material that constitutes the body 12 is biocompatible.

By way of a variant, the structure 10 forms a sports and rehabilitation equipment item or unit. For example, the structure 10 forms an assistive device having adjustable form/shape for use in strength training or rehabilitation. By way of a variant, the structure 10 forms a deployable inflatable structure for haute couture, aerospace, or for outdoor activities, such as tents, bowls or other accessories.

In yet another variant, the structure 10 forms a part of a furniture item, for example a furniture panel that is continuously deformable or a hinge that can be pneumatically activated.

In yet another variant, the structure 10 forms an industrial equipment item/unit, having an appropriate form/shape that is adapted according to use, for example a deformable headrest which adapts itself to the shape of the head, or a wind turbine blade having variable form/shape in order to optimise efficiency.

According to the invention, in each pressurized configuration, the radius of curvature of an exterior surface of the elastically deformable body 12, taken opposite each internal cavity 14 adjacent to the exterior surface, is greater than two times the size of the internal cavity 14 adjacent to the exterior surface. This property may be applicable to all of the internal cavities 14 whether or not they are adjacent to the exterior surface or, to the contrary, may not be applicable to certain of the cavities that are not adjacent to the exterior surface.

The invention claimed is:

1. A pneumatic structure comprising an elastically deformable body defining at least one network of internal cavities, each internal cavity having a closed contour in at least one section of the internal cavity, each internal cavity being configured to be pressurized so as to cause the elastically deformable body to pass from a rest configuration to at least one pressurized configuration, the elastically deformable body having in each pressurized configuration, a macroscopic metric that is distinct from a macroscopic metric in the rest configuration;

a radius of curvature of an exterior surface of the elastically deformable body, taken opposite each internal cavity adjacent to the exterior surface, is greater than two times the size of said internal cavity adjacent to the exterior surface in each pressurized configuration, wherein each internal cavity is delimited laterally, in said at least one section, by two lateral walls, by a lower region and by an upper region of the elastically deformable body, wherein said two lateral walls are part of the elastically deformable body, and wherein the elastically deformable body is produced from an elastomer-based material.

2. A structure according to claim 1, in which, in each pressurized configuration, a width of each internal cavity is less than three times a distance from the internal cavity to the exterior surface of the elastically deformable body.

3. A structure according to claim 1, in which in at least one section, the width of said internal cavity, taken between the lateral walls is less than three times a thickness of the elastically deformable body.

4. A structure according to claim 1, in which in at least one section, a thickness of the upper region or/and a thickness of the lower region, taken opposite the internal cavity is greater than half a width of the internal cavity, taken between the lateral walls.

5. A structure according to claim 1, comprising a plurality of adjacent internal cavities separated from one another by lateral walls, a length of the lateral walls being greater than the width of the internal cavity.

6. A structure according to claim 5, wherein the lateral walls extend radially in relation to a central axis, or circumferentially around a central axis.

7. A structure according to claim 1, comprising a plurality of adjacent internal cavities separated from one another by pillars, a distance between the exterior surfaces of the pillars being less than two times a thickness of the upper and lower region.

8. A structure according to claim 1, in which at least one internal cavity of the elastically deformable body is configured to receive a pressure in a range between the opposite of atmospheric pressure and four times an elastic modulus of the elastically deformable body, the elastically deformable body having a first macroscopic metric when said pressure applied is the opposite of atmospheric pressure, and a second macroscopic metric that is distinct from the first macroscopic metric when said pressure applied is four times the elastic modulus.

9. A structure according to claim 1, in which each internal cavity in each pressurized configuration has a section with an area that is less than 400% of the area of the section of the internal cavity in the rest configuration.

10. A structure according to claim 1, comprising an internal reinforcing framework deployable between a contracted state and a deployed state during the transition of the elastically deformable body passing from the rest configuration to the pressurized configuration, the internal reinforcing framework having in the deployed state an elastic modulus that is greater than an elastic modulus of the elastically deformable body in order to stiffen the elastically deformable body.

11. A structure according to claim 10, wherein a thickness of the internal reinforcing framework is at least 10 times smaller than a greatest dimension of the internal reinforcing framework.

12. A structure according to claim 10, in which the internal reinforcing framework includes a network of wires that is unstretched in the contracted state and stretched in the deployed state, or at least one tier of inextensible sheeting cut-out.

13. A structure according to claim 1, wherein the at least one network of internal cavities comprises a first network of internal cavities that is capable of being pressurized, and at least a second network of internal cavities that is capable of being pressurized independently of the first network of internal cavities.

14. A structure according to claim 13, wherein the first network of internal cavities and the second network of internal cavities are tiered.

15. A structure according to claim 1, consisting of a biomedical equipment item/unit, a recreational and/or rehabilitation equipment item/unit, a furniture component, an industrial equipment item/unit having an adaptable form or shape.

16. A production method for producing a structure according to claim 1, comprising:
   molding of a first part of the elastically deformable body having each internal cavity, with each internal cavity being open;
   closing of each internal cavity by applying a second part of the elastically deformable body over the first part of the elastically deformable body.

17. A method according to claim 16, comprising, when molding, the incorporation of an internal reinforcing framework deployable between a contracted state and a deployed state during the transition of the elastically deformable body passing from the rest configuration to the pressurized configuration, with the internal reinforcing framework in the deployed state locking-in the elastically deformable body in the pressurized configuration.

* * * * *